US007193042B1

(12) United States Patent
Cowgill et al.

(10) Patent No.: US 7,193,042 B1
(45) Date of Patent: *Mar. 20, 2007

(54) METHODS FOR PURIFYING AUTHENTIC IGF FROM YEAST HOSTS

(75) Inventors: Cynthia Cowgill, Berkeley, CA (US); Luis Juarbe-Osorio, San Francisco, CA (US); Patricio Riquelme, Walnut Creek, CA (US); Glenn Dorin, San Rafael, CA (US); Christopher M. Bussineau, Hayward, CA (US); Robert D. Kudrna, Alameda, CA (US); Carl Scandella, Bellevue, WA (US); Russell A. Brierley, West Chester, PA (US); Joan N. Abrams, Downington, PA (US); John M. Hanson, Encinitas, CA (US); Francis C. Maslanka, West Chester, PA (US)

(73) Assignees: Chiron Corporation, Emeryville, CA (US); Cephalon, Inc., West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/477,984

(22) Filed: Jun. 7, 1995

(51) Int. Cl.
*C07K 1/18* (2006.01)
*C07K 1/20* (2006.01)
*C07K 1/22* (2006.01)

(52) U.S. Cl. ............... 530/350; 530/303; 530/399; 530/408; 530/409; 514/12; 435/69.1; 435/69.4

(58) Field of Classification Search ............. 530/350, 530/399, 408, 409, 303; 514/12; 435/69.1, 435/69.4
See application file for complete search history.

(56) References Cited

U.S. PATENT DOCUMENTS

| | | | |
|---|---|---|---|
| 5,231,178 A | 7/1993 | Holtz et al. | |
| 5,288,931 A | 2/1994 | Chang et al. | ............... 530/399 |
| 5,324,639 A | 6/1994 | Brierley et al. | |
| 5,407,810 A | 4/1995 | Builder et al. | |
| 5,410,026 A | 4/1995 | Chang et al. | |
| 5,446,024 A | 8/1995 | Builder et al. | ............... 514/12 |
| 5,451,660 A | 9/1995 | Builder et al. | |
| 5,650,496 A | 7/1997 | Brierley et al. | |
| 5,695,958 A | 12/1997 | Builder et al. | ............. 435/69.1 |
| 5,712,249 A * | 1/1998 | Holloran et al. | ............... 514/12 |
| 6,117,983 A * | 9/2000 | Cowgill et al. | ............. 530/399 |

FOREIGN PATENT DOCUMENTS

EP 0 567 554 B1 11/1993

| | | |
|---|---|---|
| WO | WO 92/12993 | 8/1992 |
| WO | WO 93/11240 | 6/1993 |
| WO | WO 93/19084 | 9/1993 |
| WO | WO 95/06059 | 3/1995 |
| WO | WO 95/06064 | 3/1995 |
| WO | WO 95/16701 | 6/1995 |
| WO | WO 95/16777 | 6/1995 |
| WO | WO 96/07744 | * 3/1996 |

OTHER PUBLICATIONS

K. Axelsson et al., "Disulfide arragnement of human insulin-like growth factor I derived from yeast and plasma" *Eur. J. Biochem.* (1992) 206:987-994.
J.Y. Chang et al., "Single-Step Solubilization and Folding of IGF-1 Aggregates from *Escherichia coli*" *Protein Folding: in vivo and in vitro* (American Chemical Society, 1993) pp. 178-188.
S. Elliott et al., "Yeast-Derived Recombinant Human Insulin-Like Growth Factor I: Production, Purification, and Structural Characterization" *J. Protein Chem.* (1990) 9:95-104.
G. Forsberg et al., "Separation and characterization of modified variants of recombinant human insulin-like growth factor I derived from a fusion protein secreted from *Escherichia coli*" *Biochem. J.* (1990) 271:357-363.
R.A. Hart et al. "Effect of environment on insulin-like growth factor I refolding selectivity" *Biotechnol. Appl. Biochem.* (1994) 20:217-234.
K.R. Hejnaes et al., "Development of an optimized refolding process for recombinant Ala-Glu-IGF-I" *Prot. Eng.* (1992) 5:797-806.
S. Hober et al., "Disulfide Exchange Folding of Insulin-like Growth Factor I" *Biochem.* (1992) 31:1749-1756.
H. Meng et al., "Reduction Studies on Bacterial Recombinant Somatomedin C/Insulin-like Growth Factor" *J. Chromatog.* (1988) 443:183-192.
J.A. Miller et al., "Oxidative Refolding of Insulin-like Growth Factor I Yields Two Products of Similar Thermodynamic Stability: A Bifurcating Protien-Folding Pathway" *Biochemistry* (1993) 32:5203-5213.
L.O. Narhi et al., "role of Native Disulfide Bonds in the Structure and Activity of Insulin-like Growth Factor I: Genetic Models of Protein-Folding Intermediates" *Biochemistry* (1993) 32:5214-5221.
M. Niwa et al., "Chemical Synthesis, cloning, and Expression of Genes for Human Somatomedin C (Insulin-like Growth Factor I) and $^{59}$Val-Somatomedin C" *Ann. NY Acad. Sci.* (1986) 469:31-52.
E. Samuelsson et al. "Enhanced *in Vitro* Refolding of Insulin-like Growth Factor I using a Solubilizing Fusion Partner" *Biochemistry* (1994) 33:4207-4211.

* cited by examiner

*Primary Examiner*—Anish Gupta
(74) *Attorney, Agent, or Firm*—Alisa A. Harbin; Young J. Suh; Roberta L. Robins

(57) ABSTRACT

Methods for purifying authentic, properly folded IGF polypeptides from yeast transformants are disclosed. The methods include a refolding step and provide for high yields of authentic IGF from a variety of yeast strains.

24 Claims, No Drawings

METHODS FOR PURIFYING AUTHENTIC IGF FROM YEAST HOSTS

TECHNICAL FIELD

The present invention relates generally to the production of insulin-like growth factor (IGF) polypeptides. More particularly, the invention relates to the production of authentic, properly folded IGF from recombinant yeast hosts.

BACKGROUND OF THE INVENTION

Insulin-like growth factors (IGFS) belong to a family of polypeptides known as somatomedins. At least two IGFs are known and are termed IGF-I and IGF-II, respectively. IGFs derive their name from the fact that they are structurally and functionally similar to insulin but are antigenically distinct from insulin.

IGF-I and IGF-II share a number of structural and biological properties. Both have molecular masses of about 7,500 daltons. IGF-I has 70 amino acid residues and IGF-II has 67 residues. Rinderknecht, *J. Biol. Chem.* (1978) 253: 2769; and Rinderknecht, *FEBS Lett.* (1978) 89:283. IGF-I and IGF-II have 62% structural homology to each other. The molecules are single-chain polypeptides with three intrachain disulfide bridges. The IGFs include four peptide domains, A, B, C and D. The A and B domains are highly homologous to the corresponding domains of proinsulin and are linked by the C domain. The D domain exists as a carboxy terminal extension and a corresponding domain is not found in proinsulin. Like insulin, IGFs stimulate phosphorylation of specific tyrosine residues within the cytoplasmic domain of the receptors to which they bind. (See, e.g., WO 93/98826).

Both IGF-I and IGF-II have been isolated from human serum. The recombinant production of IGFs in bacterial and yeast hosts has also been described. For example, Chang and Swartz, *Protein Folding: in vivo and in vitro* (American Chemical Society, 1993) pp. 178–188, describe the recombinant production of IGF-I in *E. coli*. Elliott et al. *J. Protein Chem.* (1990) 9:95–104 describes the production of IGF-I in *Saccharomyces cerevisiae* using the α-factor pre-pro-leader to direct secretion of IGF-I into the culture medium. U.S. Pat. No. 5,324,639 describes the recombinant production of IGF-I in the methylotrophic yeast *Pichia pastoris*, using the *S. cerevisiae* alpha mating factor pre-pro sequence to direct secretion of the protein product.

However, attempts to purify authentic, properly folded IGF from recombinant hosts have been frustrated due to the tertiary structure of the molecule. In this regard, purification of the recombinantly produced molecule often renders a heterogenous mixture which consists largely of inactive, misfolded, insoluble and/or soluble disulfide-linked aggregates. Other aberrant molecules, such as fragments, nicked, oxidized and glycosylated forms, may also present. Thus, purification is difficult and yields of the authentic monomer are often low. See, e.g., Elliott et al. *J. Protein Chem.* (1990) 9:95–104.

Attempts have been made to correct these problems. For example, Chang and Swartz, *Protein Folding: in vivo and in vitro* (American Chemical Society, 1993) pp. 178–188, describe a method for solubilizing aggregated IGF-I produced in *E. coli*, using low concentrations of urea and dithiothreitol (DTT) in an alkaline buffer. U.S. Pat. No. 5,231,178, describes a method for the purification of correctly-folded, monomeric IGF-1 from *P. pastoris* using a combination of cation exchange, hydrophobic interaction, and gel filtration chromatography.

However, additional methods for the purification of authentic IGF from yeast would be desirable.

SUMMARY OF THE INVENTION

The present invention is based on the discovery of a method for purifying authentic, properly folded IGF polypeptides from yeast transformants. The method provides for high yields of IGF from a variety of yeast strains.

Accordingly, in one embodiment, the subject invention pertains to a method for purifying an authentic, properly folded IGF polypeptide from a yeast cell medium comprising the IGF polypeptide. The method comprises:

(a) performing a first cation exchange chromatography with the yeast cell medium to yield a first IGF mixture;

(b) denaturing and renaturing IGF species present in the first IGF mixture to yield a second IGF mixture;

(c) subjecting the second IGF mixture to hydrophobic interaction chromatography to yield a third IGF mixture; and (d) performing reverse phase high performance liquid chromatography on the third IGF mixture to yield a fourth IGF mixture, wherein the fourth IGF mixture has a greater amount of authentic, properly folded IGF than the first IGF mixture.

In another embodiment, the invention pertains to a method for refolding an IGF polypeptide derived from a yeast cell medium to yield an authentic, properly folded IGF polypeptide. The method comprises denaturing and renaturing IGF species present in an IGF mixture using a denaturation buffer comprising urea, dithiothreitol, alcohol and salt in sufficient amounts and under conditions which allow for the reduction and subsequent oxidation of disulfide bonds, thereby producing an authentic, properly folded IGF polypeptide.

In yet another embodiment, the invention pertains to a method for refolding an IGF polypeptide derived from a yeast cell medium to yield an authentic, properly folded IGF polypeptide. The method comprises denaturing and renaturing IGF species present in an IGF mixture, wherein the denaturing and renaturing are done together using a denaturation buffer having a pH of about 9 to about 11 and which comprises about 1.5 M to about 3 M urea, about 3 to about 50 mM sodium borate, about 1 M to about 1.5 M sodium chloride, about 15% to about 25% ethanol and about an equimolar to about a 5-fold molar excess of dithiothreitol. The denaturing and renaturing are conducted for about 15 to about 18 hours, at room temperature, thereby producing an authentic, properly folded IGF polypeptide.

These and other embodiments of the subject invention will readily occur to those of skill in the art in light of the disclosure herein.

DETAILED DESCRIPTION OF THE INVENTION

The practice of the present invention will employ, unless otherwise indicated, conventional methods of protein chemistry, microbiology, molecular biology and recombinant DNA techniques within the skill of the art. Such techniques are explained fully in the literature. See, e.g., *Protein Purification Methods: A Practical Approach*, (E. L. V. Harris and S. Angal, Eds., 1989); *Protein Purification Applications: A Practical Approach*, (E. L. V. Harris and S. Angal, Eds., 1990); T. E. Creighton, *Proteins: Structures and Molecular Properties* (W.H. Freeman and Company, 1993); Sambrook, et al., *Molecular Cloning: A Laboratory Manual* (2nd Edition, 1989); *Methods In Enzymology* (S. Colowick and N. Kaplan eds., Academic Press, Inc.); *Biology and Activities of Yeast* (F. A. Skinner, S. M. Passmore and R. R. Davenport eds.); *Biochemistry and Genetics of Yeast* (M. Bacila, B. L. Horecker and A. O. M. Stoppani eds.); *The Yeasts* (A. H. Rose and J. S. Harrison eds.); and *The Molecular Biology of the Yeast Saccharomyces* (Strathern et al., eds.).

All publications, patents and patent applications cited herein, whether supra or infra, are hereby incorporated by reference in their entirety.

I. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The term "insulin-like growth factor" or "IGF" as used herein encompasses both IGF-I and IGF-II and includes biologically active fragments and analogs, including C-terminal deletion muteins, and derivatives thereof that retain IGF activity and/or ability to bind IGF receptors, as described in, for example, European Publication Nos. 135, 094, 123,228, 128,733; International Publication Nos. WO 85/00831 and WO 92/04363; and U.S. Pat. Nos. 4,738,921 and 5,158,875.

An analog of IGF or an analog of the fragment includes native IGF or a fragment of native IGF that has been modified by one or more amino acid insertions, deletions, or substitutions that do not substantially affect IGF activity. Preferably, the analog has at least the same activity as the native molecule. An IGF analog also includes peptides having one or more peptide mimics ("peptoids"), such as those described in International Publication No. WO 91/04282. Furthermore, the analog can include additional modifications that do not affect activity, such as posttranslational modifications, including, e.g., glycosylation, acetylation, phosphorylation, etc., as well as additional amino acid substitutions, deletions or additions.

By "authentic, properly folded IGF" is meant a biologically active IGF polypeptide produced in a yeast host which has the same tertiary structure as a selected reference molecule. Thus, if the reference molecule is full-length, wild-type IGF-I, an authentic, properly folded, recombinantly produced IGF-I would have the same 3 intrachain disulfide bridges as found in the wild-type molecule. Similarly, if the reference molecule is an analog of IGF, the authentic, properly folded, recombinantly produced molecule would have the same intrachain bridges found in the analog. Activity can be determined as described above.

By "yeast" is meant any of the various yeasts capable of expressing a gene encoding IGF. Such yeasts include, but are not limited to, ascosporogenous yeasts (Endomycetales), basidiosporogenous yeasts and yeasts belonging to the Fungi imperfecti (Blastomycetes) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium* and *Filobasidiella*. Yeast belonging to the Fungi Imperfecti are divided into two families, Sporobolomycetaceae (e.g., genera *Sporobolomyces* and *Bullera*) and Cryptococcaceae (e.g., genus *Candida*).

Of particular interest for use with the present invention are species within the genera *Pichia, Kluyveromyces, Saccharomyces, Schizosaccharomyces, Hansenula, Torulopsis* and *Candida*, including but not limited to, *P. pastoris, P. guillerimondii, S. cerevisiae, S. carlsbergensis, S. diastaticus, S. douglasii, S. kluyveri, S, norbensis S. oviformis, K. lactis, K. fragilis, C. albicans, C. maltosa*, and *H. polymorpha*.

A "yeast host" or "yeast host cell" refers to a yeast which can be, or has been, used as a recipient for recombinant vectors or other transfer DNA. The term includes the progeny of the original yeast cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding an IGF polypeptide, are included in the progeny intended by this definition.

A "transformed" yeast cell is one which includes an exogenous polynucleotide, irrespective of the method used for insertion: for example, direct uptake, transduction, or f-mating. The exogenous polynucleotide may be maintained as a nonintegrated vector, for example, a plasmid, or alternatively, may be integrated into the host genome.

By "yeast cell medium" is meant any culture medium or solution which contains yeast cells or which contains yeast cell contents. Thus, the term encompasses media in which the yeast cell has been grown, e.g., media into which the IGF polypeptides have been secreted, including media both before or after a fermentation step. The term also encompasses buffers or reagents which contain yeast cell lysates, such as in the case where the IGF polypeptides are produced intracellularly and the yeast cells are lysed or disrupted to release the IGF polypeptides.

A composition containing A is "substantially free of" B when at least about 80% by weight of the total A+B in the composition is A. Preferably, A comprises at least about 85% to 90% by weight of the total of A+B in the composition.

II. MODES OF CARRYING OUT THE INVENTION

The present invention is based on the discovery of a purification procedure which allows for the isolation of authentic, properly folded IGF polypeptides from transformed yeast hosts. Protein yields are thereby increased due to the elimination of misfolded IGF forms. The method comprises a series of isolation steps, including a refolding step, wherein the disulfide bonds of various IGF forms present in a mixture are reduced and then reoxidized to decrease the amount of aberrant IGF forms present. Thus, the final product has more authentic IGF present than the starting material.

The IGFs of the present invention are produced recombinantly in yeast, using techniques well known in the art. See, e.g., Sambrook, et al., *Molecular Cloning: A Laboratory Manual* (2nd Edition, 1989); Elliott et al. *J. Protein Chem.* (1990) 9:95–104; and U.S. Pat. Nos. 5,231,178 and 5,324,639. For example, IGF can be produced in methylotrophic yeast transformants, such as in a protease deficient *P. pastoris* strain (see, e.g., U.S. Pat. No. 5,324,639) with the IGF coding sequence linked to a signal sequence which directs secretion and proteolytic processing of the protein product. By way of example, the present invention is described in relation to *P. pastoris* and *S. cerevisiae*. The invention, however, is not limited to these yeasts.

Expression and transformation vectors, either extrachromosomal replicons or integrating vectors, have been developed for transformation into many yeast hosts. For example, expression vectors have been developed for, among others, the following yeasts: *Saccharomyces cerevisiae*, as described in Hinnen et al. *Proc. Natl. Acad. Sci. USA* (1978) 75:1929; Ito et al. *J. Bacteriol.* (1983) 153:163; *Candida albicans* as described in Kurtz et al. *Mol. Cell. Biol.* (1986) 6:142; *Candida maltosa*, as described in Kunze et al. *J. Basic Microbiol.* (1985) 25:141; *Hansenula polymorpha*, as described in Gleeson et al. *J. Gen. Microbiol.* (1986) 132: 3459 and Roggenkamp et al. *Mol. Gen. Genet.* (1986) 202:302); *Kluyveromyces fragilis*, as described in Das et al. *J. Bacteriol.* (1984) 158:1165; *Kluyveromyces lactis*, as described in De Louvencourt et al. *J. Bacteriol.* (1983) 154:737 and Van den Berg et al. *Bio/Technology* (1990) 8:135; *Pichia guillerimondii*, as described in Kunze et al. *J. Basic Microbiol.* (1985) 25:141; *Pichia pastoris*, as described in Cregg et al. *Mol. Cell. Biol.* (1985) 5:3376 and U.S. Pat. Nos. 4,837,148, 4,929,555, 5,324,639; *Schizosaccharomyces pombe*, as described in Beach and Nurse, *Nature* (1981) 300:706; and *Yarrowia lipolytica*, as described in Davidow et al. *Curr. Genet.* (1985) 10:380 and Gaillardin et al. *Curr. Genet.* (1985) 10:49; *Aspergillus* hosts such as *A. nidulans*, as described in Ballance et al. *Biochem. Biophys. Res. Commun.* (1983) 112:284–289; Tilburn et al. *Gene* (1983) 26:205–221 and Yelton et al., *Proc. Natl. Acad. Sci. USA* (1984) 81:1470–1474, and *A. niger*, as described in Kelly and Hynes, *EMBO J.* (1985) 4:475479; *Trichoderma reesia*, as described in EP 244,234, and filamentous fungi such as, e.g, *Neurospora, Penicillium, Tolypocladium*, as described in WO 91/00357.

Control sequences for yeast vectors are known and include promoter regions from genes such as alcohol dehydrogenase (ADH), as described in EP 284,044, enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK), as described in EP 329,203. The yeast PHO5 gene, encoding acid phosphatase, also provides useful promoter sequences, as described in Myanohara et al. *Proc. Natl. Acad. Sci. USA* (1983) 80:1. Other suitable promoter sequences for use with yeast hosts include the promoters for 3-phosphoglycerate kinase, as described in Hitzeman et al. *J. Biol. Chem.* (1980) 255:2073, or other glycolytic enzymes, such as pyruvate decarboxylase, triosephosphate isomerase, and phosphoglucose isomerase, as described in Hess et al. *J. Adv. Enzyme Reg.* (1968) 7:149 and Holland et al., *Biochemistry* (1978) 17:4900. Inducible yeast promoters having the additional advantage of transcription controlled by growth conditions, include from the list above and others the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman, EP 073,657.

Yeast enhancers also are advantageously used with yeast promoters. In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region, as described in U.S. Pat. Nos. 4,876,197 and 4,880,734. Other examples of hybrid promoters include promoters which consist of the regulatory sequences of either the ADH2, GAL4, GAL10, or PHO5 genes, combined with the transcriptional activation region of a glycolytic enzyme gene such as GAP or PyK, as described in EP 164,556. Furthermore, a yeast promoter can include naturally occurring promoters of non-yeast origin that have the ability to bind yeast RNA polymerase and initiate transcription.

Other control elements which may be included in the yeast expression vectors are terminators, for example, from GAPDH and from the enolase gene, as described in Holland et al. *J. Biol. Chem.* (1981) 256:1385, and leader sequences which encode signal sequences for secretion. DNA encoding suitable signal sequences can be derived from genes for secreted yeast proteins, such as the yeast invertase gene as described in EP 012,873 and JP 62,096,086 and the a-factor gene, as described in U.S. Pat. Nos. 4,588,684, 4,546,083 and 4,870,008; EP 324,274; and WO 89/02463, as well as acid phosphatase leaders. Alternatively, leaders of non-yeast origin, such as an interferon leader, also provide for secretion in yeast, as described in EP 060,057.

The origin of replication from the 2µ plasmid origin is suitable for yeast. A suitable selection gene for use in yeast is the trp1 gene present in the yeast plasmid described in Kingsman et al. *Gene* (1979) 7:141 or Tschemper et al. *Gene* (1980) 10:157. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 Gene.

Methods of introducing exogenous DNA into yeast hosts are well known in the art, and typically include either the transformation of spheroplasts or of intact yeast cells treated with alkali cations. For example, transformations into yeast can be carried out according to the method described in Van Solingen et al. *J. Bact.* (1977) 130:946 and Hsiao et al. *Proc. Natl. Acad. Sci. USA* (1979) 76:3829. However, other methods for introducing DNA into cells such as by nuclear injection, electroporation, or protoplast fusion may also be used as described generally in Sambrook et al., cited above. Yeast cells are then cultured using standard techniques.

The IGF will either be secreted, if appropriate leader sequences are used, or produced intracellularly and the cells manipulated to allow proper isolation of an IGF-containing product.

For optimum production of recombinant IGF, a fermentation step is generally used for cell amplification. In this regard, the transformed yeast strains for use with the present invention can be grown in fermentors during the amplification stage, using standard fed batch fermentation methods. These methods will have certain common features independent of the yeast strain employed, such as a fermentation medium designed to contain adequate amounts of carbon, nitrogen, basal salts, phosphorus, and other minor nutrients (vitamins, trace minerals and salts, etc.). In addition, a growth limiting nutrient, typically carbon, will be added to the fermentor during the amplification phase to allow maximal growth.

Such methods may be adapted to a particular yeast strain due to differences in their carbon utilization pathway or mode of expression control. For example, a *Saccharomyces* yeast fermentation may require a single glucose feed, complex nitrogen source (e.g., casein hydrolyzates), and multiple vitamin supplementation. This is in contrast to the methylotrophic yeast *Pichia pastoris* which may require glycerol, methanol, and trace mineral feeds, but only simple ammonium (nitrogen) salts, for optimal growth and expression. See, e.g., Elliott et al. *J. Protein Chem.* (1990) 9:95–104, U.S. Pat. No. 5,324,639 and Fieschko et al. *Biotechnol. Bioeng.* (1987) 29:1113–1121.

For example, suitable fermentation media for use with *Saccharomyces* are described in Tables 1 and 2 of the examples. Suitable media for use with *Pichia* are described in U.S. Pat. Nos. 5,231,178 and 5,324,639 and in the table below.

Salts can be present throughout fermentation, or preferably, can be added as a single dose at the beginning of the fermentation procedure. Particularly preferred basal salts and trace salts media for *Pichia* fermentation is shown below. If this formulation is used, a single dose of the salts can be given, generally about 1–5 ml of basal salts formulation per liter of starting volume of fermentation medium will be added, more preferably about 1–3 ml per liter of medium, and most preferably 2 ml per liter will be added at the beginning of fermentation.

| Chemical | Grams/liter |
|---|---|
| BASAL SALTS | |
| Phosphoric Acid, 85% | 45.7 ml |
| Calcium Sulfate•2H$_2$O | 0.96 |
| Potassium Sulfate | 18.2 |
| Magnesium Sulfate•7H$_2$O | 14.9 |
| Potassium Hydroxide | 4.13 |
| TRACE SALTS | |
| Cupric Sulfate•5H$_2$O | 6.0 |
| Sodium Iodide | 0.08 |
| Manganese Sulfate•H$_2$O | 3.0 |
| Sodium Molybdate•2H$_2$O | 0.2 |
| Boric Acid | 0.02 |
| Cobalt Chloride | 0.5 |
| Zinc Chloride | 20.0 |
| Ferrous Sulfate•7H$_2$O | 65.0 |
| Biotin | 0.20 |
| Sulfuric Acid | 5.0 ml |

During fermentation, a variety of IGF forms are secreted into the medium, including analogs, degraded or nicked monomeric forms, oxidized and glycosylated monomers, numerous multimeric forms, such as dimers, trimers, etc., as well as a major misfolded species which is a disulfide bonded isoform of IGF. Also present is the authentic, properly folded monomeric IGF. Thus, to further enhance the yield of and purify authentic IGF polypeptides from this mixture, the following procedure can be followed.

The fermentor is harvested and cells are removed from the fermented media using standard techniques known in the art, such as by centrifugation or microfiltration or a combination of the two. For example, microfiltration using an appropriate filter will suffice to remove unwanted cellular debris.

Prior to cell removal, it may be desirable to include an alkaline shock step. The alkaline shock treatment involves addition of an alkali, such as a hydroxide of an alkali metal or an alkaline earth metal, or other suitable hydroxides that are not detrimental to the yield of the recombinant protein. An amount of the alkali is added sufficient to raise the final pH of the culture medium to between about pH 8–12, preferably, about pH 10–11. The cells are exposed to the alkaline shock for a period ranging from about 30 minutes to about 10 hours, preferably, about 1 hour to about 8 hours, and more preferably from about 2 to 4 hours. The culture temperature can be maintained in a range of about 25 degrees C. to about 35 degrees C. Additions of thiols prior to or during the alkaline shock step can enhance the yield of IGFs. An amount of thiol added can be in the range of between about 0.05 mM to about 50 mM.

Once cells and debris are removed, the pH of the cell-free fermentation broth can be adjusted to about pH 3–7, more preferably about pH 3–4, and loaded onto a cation exchange column to capture the IGF species present in the fermentation medium, including the aberrant and authentic forms. Cation exchange also serves to eliminate some yeast contaminants. An additional filtration step, using e.g., a polypropylene depth filter, can be used prior to cation exchange chromatography.

Suitable cation exchangers include a wide variety of materials, known in the art. Particularly preferred are strong cation exchangers capable of binding IGF polypeptides over a wide pH range. For example carboxymethylated and sulfonated cation exchange matrices are particularly useful for use herein. Useful matrix materials include but are not limited to, cellulose matrices, such as fibrous, microgranular and beaded matrices; agarose, dextran, polyacrylate, polyvinyl, polystyrene, silica and polyether matrices; and composites. Particularly preferred herein are matrices containing the functional ligand R—SO$_3^-$, preferably sulfopropyl resins. Representative matrices include TosoHaas Toyopearl SP550C and Merck Fractogel EMD SO$_3^-$-650 (m).

Prior to loading the fermentation medium, the cation exchange matrix can be equilibrated using several column volumes of a dilute, weak acid (e.g., four column volumes of 20 mM acetic acid, pH 3). Following equilibration, the fermentation medium is added and the column can be washed one to several times, prior to elution of the IGF species, also using a weak acid solution such as a weak acetic acid or phosphoric acid solution. For example, approximately 2–4 column volumes of 20 mM acetic acid, pH 3, can be used to wash the column. Additional washes, using e.g., 2–4 column volumes of 0.05 M sodium acetate, pH 5.5, or 0.05 M sodium acetate mixed with 0.1 M sodium chloride, pH 5.5, can also be used.

Following adsorption of the IGF molecules to the cation exchanger, the IGF polypeptides are eluted by contacting the matrix with a buffer having a sufficiently high pH or ionic strength to displace the IGF polypeptides from the matrix. For example, a 0.05 M sodium acetate, 0.4 M sodium chloride solution at pH 5.5 can be used. Another exemplary elution buffer includes a buffer having 0.1 M potassium borate, 0.6 M potassium chloride, 0.1 mM EDTA, pH 8.7. However, other buffers, known to those of skill in the art, will also find use herein. The quantity of elution buffer can vary widely and will generally be in the range of about 2 to 10 column volumes. Following elution, the eluate can be assayed for total IGF concentration.

Following the cation exchange step, or optionally, during or just subsequent to fermentation, a refolding step can be conducted to convert aberrant multimeric IGF forms to authentic IGF, thereby enhancing the yield of authentic IGF by as much as two- to three-fold or more. Several methods for producing authentic, properly folded IGF from aggregated incorrectly folded forms via a refolding step are known to those of skill in the art. See, e.g., Hart et al. *Biotechnol. Appl. Biochem.* (1994) 20:217–234; Chang and Swartz, *Protein Folding: in vivo and in vitro* (American Chemical Society, 1993) pp. 178–188; Miller et al. *Bio-* chemistry (1993) 32:5203–5213; Newa et al. *Ann. NY Acad. Sci.* (1986) 469:31–52; and Meng et al. *J. Chromatog.* (1988) 443:183–192. Such methods generally include the use of a denaturation buffer, e.g., a sodium borate or sodium carbonate buffer, which includes denaturing agents, such as urea or guanidine hydrochloride, and/or a thiol, e.g., DTT, glutathione, β-mercaptoethanol, monothioglycerol, and mercaptoacetic acid, to reduce existing disulfide bridges. Other buffers which will accommodate disulfide bond exchange can also be used. A salt, such as any conventional salt solution, including sodium chloride, potassium chloride, etc. and an alcohol, such as ethanol, propanol, butanol, etc. will also be present.

A particularly preferred method for the reduction of aberrant disulfide bonds includes the use of a buffer which comprises high concentrations of urea, e.g., about 1 M to about 4 M, preferably about 1.5 M to about 3 M, and most preferably about 2 M, combined with about 1 mM to about 75 mM sodium borate, more preferably about 3 to about 50 mM sodium borate, most preferably 50 mM sodium borate; 0.5 to about 3 M sodium chloride, more preferably 1 to about 1.5 M sodium chloride; 10% to about 30% ethanol, more preferably 15% to about 25% ethanol; about 0.5- to about 7-fold molar excess of DTT, more preferably about an equimolar amount to about a 6-fold molar excess, and preferably about an equimolar amount to about a 5-fold molar excess of DTT. The amount of reducing agent is not critical, however, the more of the agent added, the longer reoxidation will take. The final pH of the buffer is about 8 to 12, more preferably about 9 to about 11. A carbonate buffer instead of the sodium borate buffer can also be used. The reaction is allowed to proceed for several hours, e.g., for about 8 to about 24, more preferably 15 to about 18 hours, at room temperature, during which time denaturation, reshuffling of the disulfide bonds, and renaturation occur.

The product can be dialyzed, e.g., using diafiltration, to remove the refolding reagents and to avoid precipitation when the pH is adjusted, especially if refolding has been done in a carbonate buffer. Diafiltration is normally performed using e.g., a sodium borate or carbonate buffer. The pH of the solution is adjusted to be acidic, e.g., adjusted to pH 1.5 to about 5, preferably 2 to about 4, using e.g., HCL. Following refolding (or following the cation exchange step if the refolding has been done prior to cation exchange) further ultrafiltration, diafiltration and salt precipitation steps can be performed to remove high molecular weight contaminants and to enhance the binding affinity of IGF for a hydrophobic interaction chromatography (HIC) matrix. Salt precipitation is generally done using any of various salts, such as, but not limited to sodium sulfate, potassium sulfate, ammonium sulfate, potassium phosphate, sodium acetate, ammonium acetate, sodium chloride, sodium citrate, and the like, using a salt concentration of about 0.2 M to about 2 M, more preferably about 0.3 to about 1 M. Ammonium sulfate is especially preferred at a concentration of about 0.5 M to about 1 M.

Hydrophobic interaction chromatography (HIC) is then performed on the recovered product. This step decreases glycosylated and oligomeric species and substantially reduces yeast contaminants. Suitable HIC matrices include alkyl- or aryl-substituted matrices, such as butyl-, hexyl-, octyl- or phenyl-substituted matrices, including agarose, cross-linked agarose, sepharose, cellulose, silica, dextran, polystyrene, poly(methacrylate) matrices, etc. Particularly preferred HIC matrices include a a mixed mode resin, such as a polyethyleneamine resin, such as Amicon silica-PAE 1000 L granular, 50 micron bead matrix, or a butyl- or phenyl-substituted poly(methacrylate) matrix, such as Toso-Haas Toyopearl Butyl 650M matrix and TosoHaas Toyopearl Phenyl 65µ resin, respectively.

Prior to loading, the column is equilibrated using standard buffers, such as an acetic acid/sodium chloride solution or HEPES containing ammonium sulfate, and the column loaded with the sample. The column is then washed using standard buffers and under conditions such as those described above. IGF can be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient, using e.g., a gradient of ammonium sulfate, can also be used to elute the IGF molecules. The eluant is then optionally concentrated, e.g., by filtration such as diafiltration or ultrafiltration. Diafiltration eliminates ammonium sulfate and decreases conductivity.

An additional cation exchange chromatography step can then performed to further decrease the amount of glycosylated species. However, this step is not necessary, especially if the yeast host is *P. pastoris*. Suitable cation exchange matrices are as described above. Prior to loading, the column is equilibrated, also as described above. IGF species are eluted using standard buffers, such as a bicine buffer which includes about 50 to 100 mM bicine, more preferably about 75 mM bicine; 25 to about 100 mM sodium chloride, preferably about 50 mM sodium chloride, and about 0.05 to about 0.5 EDTA, preferably about 0.1 mM EDTA, pH 7.5.

Reverse phase high pressure liquid chromatography (RP-HPLC) is then performed on the mixture to remove contaminants, such as met-oxidized, glycosylated, nicked, degraded and misfolded species, including a des2-IGF species. In this regard, silica derivatized resins, with alkyl functionalities, typically $C_4$ to $C_{10}$, more preferably $C_6$ to $C_9$ and most preferably $C_8$, resins will find use. A polymeric resin can also be used, such as TosoHaas Amberchrome CG1000sd resin. The column can be washed with a solvent, such as ethanol, e.g., at a concentration of 15% to about 25%.

A suitable elution buffer, containing an organic solvent such as methanol, propanol, tetrahydrofuran, acetonitrile or ethanol, will find use for eluting the authentic IGF polypeptides. Elution can be performed using one or more gradients or isocratic conditions, with gradient conditions preferred to reduce the separation time and to improve resolution. Generally, the gradient is from about 5% to about 80% (v/v) solvent in water, more preferably from about 5% to about 60% (v/v) and most preferably from about 10% to about 50% (v/v) solvent in water. A particularly preferred method involves the use of two gradients, the first of which is from about 10% to about 25% solvent, more preferably about 14% to about 22% solvent. The second gradient is about 20% to about 30% solvent, more preferably about 22% to about 26% solvent. Particularly preferred elution buffers for use herein include ammonium acetate, acetonitrile solutions, pH 6.7.

A final filtration step, using e.g., gel filtration, ultrafiltration, and the like, can be performed on the RP-HPLC product to remove any excess salts and to replace the buffer with a suitable buffer for formulation of the final drug product. The filtered product can also be concentrated using diafiltration, lyophilization, etc.

The yield of IGF polypeptides, including authentic IGF, can be monitored at each step described above using any of several reverse phase high pressure liquid chromatography columns, such as cyano RP-HPLC, $C_4$ RP-HPLC, $C_8$ RP- HPLC; as well as cation exchange HPLC and size exclusion HPLC. Purity can be determined using standard techniques such as SDS-PAGE, or by measuring non-IGF proteins using Western blot and ELISA assays. For example, polyclonal antibodies can be generated against proteins isolated from a negative control yeast fermentation and the cation exchange recovery. The antibodies can be used to probe for the presence of contaminating host cell proteins.

Typically, the yield of IGF polypeptides at each step will be about 50% or more, more preferably about 60% to about 80% or more. For example, the first cation exchange step typically provides about 90% recovery which includes all IGF species, of which about 10% is authentic, properly folded IGF. The refolding step typically increases the amount of authentic IGF by 2- to 3-fold. The hydrophobic interaction chromatography step generally provides about 80% to 90% recovery, the second cation exchange step about 80% recovery and the RP-HPLC column about 90% to 95% recovery.

Once purified, the authentic, properly folded IGF can be used for a variety of purposes. In this regard, the IGF can be used, e.g., to stimulate growth of cells in vitro in a variety of tissues and cell types. The purified IGFs can also be formulated into pharmaceutical compositions and used, e.g., for bone repair and replacement therapy, to treat osteoporosis, to inhibit an inflammatory response, ischemic injury, and organ rejection upon transplantation, and to increase lactation and meat production in cattle and other farm animals.

Below are examples of specific embodiments for carrying out the present invention. The examples are offered for illustrative purposes only, and are not intended to limit the scope of the present invention in any way.

EXAMPLE I

Production of Recombinant IGF in *S. cerevisiae*

Recombinant human IGF-I protein (rhIGF-I) was expressed in *S. cerevisiae* strain JSC417, transformed with plasmid pYLUIGF1-24. The yeast strain JSC417, was deposited with the American Type Culture Collection (ATCC) located at 12301 Parklawn Drive, Rockville, Md. 20852, on Aug. 2, 1994 with ATCC Accession No. 74295. Strain JSC417 was derived from strain AB110. JSC417 has the following genotype: Matα, ura 3-52, leu 2, pep 4-3, his 4-580, [cir °].

Expression of rhIGF-I in *S. cerevisiae* strain JSC417 was non-constitutive and under the regulation of a hybrid ADH2-GAP promoter derived from promoter sequences of yeast alcohol dehydrogenase, as described in Beier, *Nature* (1982) 300:724, and glyceraldehyde-3-phosphate dehydrogenase, as described in EP 120,551. In addition, the rhIGF-I sequences were fused to the yeast α-factor leader which allowed for secretion, and to the yeast α-factor terminator, both as described in Brake, *Proc. Natl. Acad. Sci.* (USA) (1984) 81:4642. Induction of rhIGF-I xpression was achieved by maintaining low concentrations of glucose in the growth medium during fermentation.

Plasmid pYLUIGF1-24 is a yeast expression vector which contains the sequence coding for rhIGF-I cloned into the BamHI site of vector pAB24, as described in Barr, *Bio/Technology* (1987) 5:486, as well as pBR322 sequences including the ampicillin resistant (ampR) gene, 2-micron (2μ) sequences, and the yeast LEU 2 and URA 3 genes. The expression cassette for rhIGF-I consisted of (5' to 3') ADH2 regulatory sequences, a GAP promoter, α-factor leader, a rhIGF-I synthetic gene and α-factor terminator, as described in EP 123,228.

The rhIGF-I gene cloned into the expression cassette was chemically synthesized using the phosphoramidite procedure as described by Urdea, *Proc. Natl. Acad. Sci.* (USA) (1983) 80:7461, and according to the Dayhoff amino acid sequences.

*S. cerevisiae* cells were transformed with plasmid pYLUIGF1-24 following a standard protocol as described in Hinnen, *Proc. Natl. Acad. Sci.* (USA) (1978) 75:1929. Briefly, the transformation mixture was plated onto uracil-deficient selective plates that were yeast nitrogen base with amino acids containing 2% glucose. The plates were incubated for four days at 30° C. Transformant colonies were transferred into leucine-deficient, selective media with 8% glucose, and grown at 30° C. Expression of rhIGF-I was accomplished by growing the yeast transformants in uracil-deficient medium with 4% glucose at 30° C. for 48 hours. Expression of rhIGF-I in the medium at 48 hours was analyzed by several methods including RP-HPLC, SDS-PAGE, RIA, or radioreceptor assay.

Production of rhIGF-I involved successive amplification of the yeast cells contained within the seedstock aliquot. The first amplification stage was carried out in shake flasks at a controlled temperature of about 30° C. in a rotary shaker-incubator. Approximately $10^7$ cells were thawed into about 500 mL of uracil- and leucine-deficient media, as described above, containing 5–8% glucose. After about 35±2 hours, the flask contents were transferred to a small fermentation vessel for the second stage of cell amplification. This culture was grown for about 24±4 hours under controlled temperature with aeration (1 vvm) and agitation (400–600 rpm) in 10 L of the same media used for stage I. 10–30 L of the stage II culture was transferred to a larger, production-scale fermentation vessel (10,000 L) for the final amplification and rhIGF-I expression phase of growth. Stage III utilized a semi-defined growth media containing casein hydrolyzate, basal salts, vitamins, trace elements, and antifoam. The casein hydrolyzate employed may be any commercial brand with a composition of at least 5% amino-nitrogen, at least 10% total nitrogen, not more than 20% ash, but preferably would have a composition comparable to that of N-Z-Amine HD (Quest). The antifoam employed may be any of several commercially available polyalcohol- or silicon-based compounds. The media used is listed in Tables 1 and 2 below. The fermentation was carried out at constant 30° C., pH 6 (by addition of 50% sodium hydroxide or 75% phosphoric acid), aeration (0.8 vvm), pressure (5–12 psig), and glucose feed rate with constant agitation. The fermentation is known to those skilled in the art as a fed-batch mode of operation, so-called because the fermentor is initially filled to less than capacity (for example approximately 50%), allowing for the addition of a suitable amount of a glucose feed solution with a concentration of about 25–50% (w/v). For a media composition described as low range in Tables 1 and 2, for example, 800–900 kg glucose was added to the fermentor over the duration of the run at a rate of addition that depends on yeast cell density and residual glucose concentration. Typically, glucose was added at about 500 g/min for approximately the first 26 h, at about 1000 g/min for approximately the next 24 h, and finally at about 500 g/min until completion. Cell growth concomitant with product expression occurs once the media becomes depleted of excess glucose, and may continue until the culture reaches the desired cell density of approximately 35 gDCW/L (grams dry cell weight per liter). If the media composition is greater than that given in the low range of Tables 1 and 2, the rate of addition of glucose, for example, may be increased to about 1500 g/min after the first 24 hours of fermentation. The high range media composition may support higher cell densities of approximately 100 gDCW/L.

TABLE 1

| Ingredients | Amount (g/10 L Final Volume) Low Range | Intermediate Low Range 2 × g/10 L | Intermediate High Range 3 × g/10 L | High Range 4.5 × g/10 L |
|---|---|---|---|---|
| casein hydrosylate (CAA) | 260.00 | 520.00 | 780.00 | 1170.00 |
| Glucose | 875.00 | 1750.00 | 2625.00 | 3937.50 |
| $NH_4SO_4$ | 50.00 | 100.00 | 150.00 | 225.00 |
| $KH_2PO_4$ | 10.00 | 20.00 | 30.00 | 45.00 |
| $MgSO_4 \cdot 7H_2O$ | 5.00 | 10.00 | 15.00 | 22.50 |
| NaCl | 1.00 | 2.00 | 3.00 | 4.50 |
| $CaCl_2 \cdot 2H_2O$ | 1.00 | 2.00 | 3.00 | 4.50 |

TABLE 2

| Ingredients | mg Low Range | Intermediate Low Range 2 × mg | Intermediate High Range 3 × mg | High Range 4.5 × mg |
|---|---|---|---|---|
| Na—Mo•2 $H_2O$ | 0.82 | 1.64 | 2.46 | 3.69 |
| $H_3BO_3$ | 2.05 | 4.10 | 6.15 | 9.225 |
| $CuSO_4 \cdot 5 H_2O$ | 0.16 | 0.32 | 0.48 | 0.72 |
| KI | 0.41 | 0.82 | 1.23 | 1.845 |
| $FeCl_3 \cdot 6 H_2O$ | 0.82 | 1.64 | 2.46 | 3.69 |
| $MnSO_4 \cdot H_2O$ | 1.64 | 3.28 | 4.92 | 7.38 |
| $ZnSO_4$ | 1.64 | 3.28 | 4.92 | 7.38 |
| pantothenate | 323.00 | 646.00 | 969.00 | 1453.50 |
| myo-inositol | 323.00 | 646.00 | 969.00 | 1453.50 |
| thiamine | 23.20 | 46.40 | 69.60 | 104.40 |
| pyridoxine | 23.20 | 46.40 | 69.60 | 104.40 |
| biotin | 1.55 | 3.10 | 4.65 | 6.975 |
| PABA | 15.46 | 30.92 | 46.38 | 69.57 |
| riboflavin | 15.46 | 30.92 | 46.38 | 69.57 |
| folic acid | 1.55 | 3.10 | 4.65 | 6.975 |
| niacin | 23.20 | 46.40 | 69.60 | 104.40 |

EXAMPLE II

Production of Authentic, Properly Folded IGF-I

A. Recombinant IGF-1 was also recovered from *S. cerevisiae* and *P. pastoris*, using the following technique. IGF-I protein was expressed in *S. cerevisiae* strain JSC417 as described above. *P. pastoris* was transformed with a plasmid encoding IGF-1 using standard techniques, e.g., as described in U.S. Pat. No. 5,324,639. Following fermentation, the media was recovered by centrifuging the broth and the pH of the supernatant adjusted to pH 4 and then microfiltered/diafiltered. The resulting filtrate was loaded onto an EMD Fractogel $SO_3$-650 column (10–20 mg/ml resin) to perform the first cation exchange chromatography. The column had been equilibrated previously with 4 CVs (column volumes) of 20 mM acetic acid, pH 3. After the load was finished, the column was washed with 20 mM acetic acid pH 3 until the A280 signal dropped to baseline (~2–3 CVs).

The IGF-1 species were eluted with a 0.1 M potassium borate, 0.6 M potassium chloride, 0.1 mM EDTA, pH 8.7 wash, at a linear flow rate of 120–200 cm/hr. The whole peak was collected until the A280 dropped to baseline (~3–4 CVs). Following elution, the column was cleaned with a 1 M potassium hydroxide solution (2 CVs) and held for 1–2 hours. The column was then washed with 4–6 CVs of water and reequilibrated with 20 mM acetic acid, pH 3. The eluate was immediately assayed for total IGF-1 concentration and prepared for the refolding reaction.

The load for this column can also be a pH-shocked, standard density cell culture supernatant. In that case, the pH shock was performed at pH 10.5 for 2–4 hours, using 50% sodium hydroxide to raise the pH of the whole culture. The whole yeast were separated from the product-containing spent media by continuous centrifugation. After collection, the pH of the supernatant was readjusted to pH 4 with about 75% phosphoric acid, and then microfiltered/diafiltered prior to loading the column.

Refolding was then conducted as follows. The pool from the fractogel column was diluted to 1.5 mg/ml total IGF (0.067 mM), based on the reduced HPLC assay, into the following buffer: 50 mM sodium borate, pH 10.5, 2 M urea 1 M sodium chloride, 10 mM EDTA, 20% ethanol, and DTT 5-fold molar excess (0.335 mM). The reaction mixture was stirred very gently for 15–18 hours at room temperature. A lower DTT molar excess can be used for the more pure *P. pastoris* feedstock.

Following refolding, diafiltration was done to eliminate refolding salts and to avoid precipitation upon pH drop. Diafiltration was done using a Filtron membrane assembly, 3×0.75 ft$^2$, 1 K MWCO. (A 3K membrane can be used instead of a 1K, with a slight decrease in yield (5–10%)). The refold pool was concentrated 10-fold. The pool was diafiltered into 50 mM sodium borate, pH 10–10.5, with 4 volume equivalents. The pH was adjusted to 2.5–3.0 with 6 N HCl and the pool was then diafiltered into 100 mM acetic acid, pH 4, using 4 volume equivalents. The final diafiltered pool can be stored at 4 degrees C. as a stable hold pool, or alternatively, can be prepared as the load for the HIC step.

The diafiltered pool (100 mM acetic acid, pH 4) was combined with 1 part 200 mM HEPES, 10 mM EDTA, pH 8, and 2 parts water, for a final 1 in 4 dilution of the pool with a final 50 mM HEPES concentration. (The diafiltered pool load can be diluted 1 in 3 instead of 1 in 4 before addition of the ammonium sulfate and still have similar binding to the column bed.) Ammonium sulfate was added to a final concentration of 1 M, and the mixture was stirred at room temperature for at least 1 hour. Precipitates were removed by centrifugation.

HIC chromatography was then conducted on the supernatant using an Amicon silica-PAE 1000 L granular resin, 50 micron beads (load was 5–15 mg/ml resin). (other variations of the resin were also tried including 300 L-40 micron spherical and the high pressure 10 micron 1000 L.) The column was pre-equilibrated with 50 mM HEPES, 2.5 mM EDTA, 1 M ammonium sulfate, pH 8 (6 CVs). The column was washed with 10 CVs of equilibration buffer. The linear flow rate was 100–150 cm/hr. Product was eluted with 5–7 CVs (until A280 dropped to baseline) of 50 mM HEPES, 2.5 mM EDTA, 0.5 M ammonium sulfate, pH 8. The column was washed with 4 CVs of water and the column was stripped with 2 M NaCl in pH 8 buffer (50 mM Tris or HEPES). The column can also be stripped with 0.1 M sodium hydroxide, but the addition of 5 mM aluminum nitrate or aluminum chloride is necessary for the protection of the silica backbone.

Variations in the protocol were necessary to accommodate higher pressure drops, higher selectivities or higher binding capacities for different cases. For higher resolution of the glycosylated species from the native IGF-1, a gradient was run instead of using the step elution. This required higher buffer utilization, longer processing time, and a slightly more involved procedure.

The product can also be eluted with the loading buffer of the next column step (100 mM acetic acid, 0.1 mM EDTA) to avoid the following diafiltration, but the purity of the eluate is then reduced.

The PAE pool from above was diafiltered using a Filtron membrane assembly, 3×0.75 ft$^2$, 1 K MWCO, with 4 volume equivalents, into 100 mM acetic acid, 0.1 mM EDTA. This step can be eliminated if the PAE column is eluted with the SP-650S loading buffer (see below) instead of with the 0.5 M ammonium sulfate buffer.

After diafiltration, a second cation exchange column was run on the S. cerevisiae product. This step was not used with the P. pastoris product. The resin used was Toyopearl SP-650S, 35 micron bead and the linear flow rate was 77 cm/hr. Loading was 16 mg/ml. Prior to loading, the column was equilibrated with 10 CVs of 100 mM acetic acid, 0.1 mM EDTA. The column was washed with 5 CVs of 100 mM acetic acid, 0.1 mM EDTA (until conductivity dropped to baseline). A pH wash was done with 5 CVs of 75 mM bicine, 0.1 mM EDTA, pH 7.5 and IGF-1 eluted using 10 CVs of 75 mM bicine, 50 mM sodium chloride, 0.1 mM EDTA, pH 7.5. (The concentration of salt in the elution buffer (50 mM sodium chloride) can be dropped to 25 mM, with an equally effective separation.) 0.25 CV fractions were collected and analyzed by cyano RP-HPLC for purity (fractions were pooled such that the resulting overall glycosylated IGF-1 level was 8% or less). The column was washed with 5 CVs of 75 mM bicine, 1 M sodium chloride, 0.1 mM EDTA, pH 7.5 and the column cleaned with 5 CVs of 0.15 N sodium hydroxide, followed by 5 CVs of water.

The pooling criteria can be modified to increase or decrease the levels of glycosylated species in the pool, with concomitant increase or decrease in yield, respectively, for this step.

The SP-650S pool (or in the case of the P. pastoris produced product, the diafiltered PAE pool) was then prepared for RP-HPLC by filtering through a 0.2 micron filter, and diluting the load with an equal volume of Buffer A (Buffer A is 0.18 M ammonium acetate, 10% acetonitrile, pH 6.7). The buffer was adjusted for pH prior to organic addition. The load was allowed to equilibrate with the organic solvent for two hours at room temperature. The resin used was Eka Nobel Kromasil C8, 10 micron bead. Load was 15 mg/ml.

The column was equilibrated with 1.5–2 CVs of Buffer A and then with 90% Buffer A/10% Buffer B (Buffer B is 010 M ammonium acetate, 50% acetonitrile, pH 6.7) over 3–4 CVs. Buffer B was adjusted for pH prior to organic addition. The final pH of Buffer B was typically higher than 6.7. The SP-650S pool was loaded. The load line was flushed with Buffer A and the following gradient run, collecting 0.25 CV's fractions:

From 10% B to NMT 30% B in NMT 25 minutes;
Maintain % B for 5 minutes;
Increase the % B by 0.1%/min for 100 minutes;
After the peaks elute, go to 80% B; and maintain for 5–10 minutes.

Fractions were pooled based on the purity as calculated by cyano RP-HPLC (goal of >95% overall purity). The column was cleaned by washing with 2–4 Vs of 80% acetonitrile.

The level of met-oxidized/glycosylated species in the load affects the final overall purity of the pool and the capacity of the column. Capacities up to 50 mg/ml were observed if the level of these species was down to about 5%.

The total IGF titer after fermentation was 150–200 mg/L using S. cerevisiae and 800–1200 mg/L using P. pastoris. Final yield of authentic IGF-1 using this process was about 40 mg/L of fermentation medium for the S. cerevisiae isolated product and about 100–120 mg/L of fermentation medium for the P. pastoris isolated product. The overall purity (authentic IGF-1/total IGF-1 species) was 95–97%.

B. Authentic IGF-1 was also recovered using the procedure described above with the following modifications.

Following fermentation, the filtrate was used in a first cation exchange reaction done on a TosoHaas Toyopearl SP550C resin. After loading, the column was washed with approximately 3.5 CVs of 0.02 M acetic acid and then with 3.5 CVs of 0.05 M sodium acetate, 0.1 M sodium chloride, pH 5.5. The product was eluted using approximately 4 CVs of 0.05 M sodium acetate, pH 5.5.

Refolding was done by diluting the cation exchange recovery pool into a buffer consisting of 2 M urea, 1.5 M sodium chloride, 15% ethanol, 5 mM sodium borate and 0.2 mM DTT, pH 9–9.5. Refolding was carried out at room temperature for 15–20 hours.

HIC was carried out using a TosoHaas Toyopearl Butyl 650M column without ammonium sulfate in order to avoid potential problems that might be caused by precipitation. The pH of the refold pool was reduced to approximately 4.2 with acetic acid and diluted with an equal volume of 1 M sodium chloride prior to loading. After loading, the column was washed with approximately 3 CVs of 0.2 M acetic acid, 0.5 M sodium chloride, pH 3.0. The column was then washed with approximately 10 CVs of 0.2 M acetic acid, 0.25 M sodium chloride, pH 3.0. The column was eluted with approximately 4 CVs of 0.2 M acetic acid, 0.2 M sodium chloride, pH 3.0.

The second cation exchange step was conducted using a TosoHaas Toyopearl SP550C resin. The column was equilibrated with 0.05 M sodium acetate, pH 5.5 buffer. After loading, the column was washed with approximately 1 CV of 0.05 M sodium acetate, pH 5.5 buffer and then with approximately 7 CVs of 0.05 M sodium acetate, 0.1 M sodium chloride, pH 5.5 buffer. The product was eluted with approximately 7 CVs 0.05 M sodium acetate, 0.4 M sodium chloride, pH 5.5. buffer.

RP-HPLC was conducted using a TosoHaas Amberchrome CG1000sd resin. The product was loaded onto the column under aqueous conditions and washed with a 0.2 M acetic acid buffer. The product was eluted using a 19% ethanol isocratic wash, followed by a gradient to 25% ethanol. The separation of less hydrophobic IGF forms (i.e., oxidized, glycosylated and some degraded IGF forms) from authentic IGF occurs during the 19% ethanol wash, and the remainder of the product is eluted from the column in the gradient while more hydrophobic forms (i.e., multimeric and other degraded IGF forms) are retained on the column. The column was then stripped with a high concentration of ethanol (70–100%).

The product was then concentrated using a Filtron 1000 MW polysulfone flat membrane and 0.1 M acetic acid. The product can also be concentrated using an AG Technology 5000 MW polysulfone hollow fiber membrane. Such membranes have a higher flux rate and better IGF retention capability than the flat membranes.

The total IGF titer using this process was 800–1200 mg/L. The final yield of authentic IGF-1 using this process was about 100 mg/L of fermentation medium. The overall purity (authentic IGF-1/total IGF-1 species) was about 94%.

C. Authentic IGF-1 was also recovered from *S. cerevisiae* using the following procedure which did not include a refold step. IGF-I protein was expressed in *S. cerevisiae* strain JSC417 as described above. Fermentation and pH shock reaction were performed as described above in Example IIA. After collection, the pH of the supernatant was readjusted, with about 75% phosphoric acid, and filtered using microporous tangential flow filtration prior to adsorbing on a cation exchange resin. The column was washed with 20 mM acetic acid and 100 mM potassium borate/0.1 mM EDTA buffers, and eluted with a 100 mM potassium borate/0.1 mM EDTA/300 mM potassium chloride buffer at pH 8.7.

Following the cation exchange step, the pH of the eluate was adjusted to pH 4 and salt precipitation performed to remove high molecular weight contaminants. Precipitation was conducted in the cold using 0.5 M ammonium sulfate, 5% acetonitrile, 2.5 mM EDTA, for 4–24 hours. Filtration was then done using an AG Tech 23 sq. ft, 0.22 micron hollow fiber filter in tandem with a Waukesha pump. The permeate was collected in one tank with precipitated material retained in the original tank. A final salt wash was conducted using approximately 10 liters of a solution of 0.5 M ammonium sulfate, 50 mM sodium acetate, 2.5 mM EDTA, pH 4.

HIC was then conducted using the sample from the previous precipitation step on a Sepragen 50 L Superflow Radial Flow column and TosoHaas, Phenyl 65 micron, HIC resin with a flow rate of 10 L/min as follows. Elution was conducted using a linear gradient from 0.9 M ammonium sulfate to 0.5 M ammonium sulfate.

Ultrafiltration and diafiltration were performed on the pool from the above column. For ultrafiltration, the start material was diluted in 0.7 M ammonium sulfate, pH 6.7. The load was prepared by titrating to below pH 4 with glacial acetic acid. The filtration system used was an AG Tech 36 sq. ft, 5,000 MWCO hollow fiber filter in tandem with a Waukesha pump and nitrogen overlay. Maximum working process circuit volume was eight liters. Typically, six liters were used. Diafiltration was conducted with approximately 20 liters of water for injection (WFI), followed by 20 mM acetic acid until the permeate pH was 3.5 (approximately 30 liters).

RP-HPLC was then conducted using a Prochrom LC150, 15 centimeter diameter high pressure column with a six liter volume and a Kromasil, $C_8$, 10 micron resin. The flow rate was 1 liter per minute. The column was equilibrated in 14% acetonitrile by mixing Buffer A, which consisted of 0.18 M ammonium acetate, 10% acetonitrile, pH 6.7 and Buffer B, which consisted of 0.10 M ammonium acetate, 50% acetonitrile, pH 6.7. The load was prepared by diluting 1:1 with Buffer A. Elution was conducted using a linear gradient of 14% to 22% acetonitrile buffer solutions. The column was held constant at 22% before a second linear gradient was run from 22% to 26% acetonitrile which eluted the product.

Finally, another ultrafiltration/diafiltration step was done. Ultrafiltration was conducted on the RP-HPLC pool using a Hoescht 50 sq.ft, 4,000 MWCO hollow fiber filter in tandem with a Waukesha pump and nitrogen overlay. Maximum working process circuit volume was eight liters. Typically, six liters were used. The load was prepared by dilution with 3 parts 20 mM acetic acid. Diafiltration was done using approximately 40 liters of 20 mM acetic acid.

The total IGF titer using this process was 25–40 mg/L. The final yield of authentic IGF-1 using this process was about 5 mg/L of fermentation medium.

Thus, methods for purifying authentic, properly folded IGF polypeptides from yeast hosts are disclosed. Although preferred embodiments of the subject invention have been described in some detail, it is understood that obvious variations can be made without departing from the spirit and the scope of the invention as defined by the appended claims.

What is claimed is:

1. A method for isolating an authentic, properly folded insulin-like growth factor (IGF) polypeptide from a medium into which the IGF polypeptide has been secreted by *Pichia pastoris* cells expressing the IGF polypeptide, wherein the method comprises:
   (a) performing a cation exchange chromatography with the medium to yield a first IGF mixture;
   (b) denaturing and renaturing IGF species present in the first IGF mixture to yield a second IGF mixture;
   (c) subjecting the second IGF mixture to hydrophobic interaction chromatography to yield a third IGF mixture; and
   (d) performing reverse phase high performance liquid chromatography on the third IGF mixture to yield a fourth IGF mixture, wherein the fourth IGF mixture has a greater amount of authentic, properly folded IGF than the first IGF mixture, and further wherein only one cation exchange step is performed in the method.

2. The method of claim 1, wherein the method further comprises raising the pH of the yeast cell medium which comprises yeast cells to about pH 8 to about pH 12, prior to the first cation exchange chromatography.

3. The method of claim 2, wherein the method comprises raising the pH of the yeast cell medium which comprises yeast cells to about pH 10 to about pH 11, prior to the first cation exchange chromatography.

4. The method of claim 1, wherein the first cation exchange chromatography is performed using a sulfopropylated matrix.

5. The method of claim 1, wherein the denaturing and renaturing steps are performed together using a denaturation buffer comprising urea, dithiothreitol, alcohol and salt, in sufficient amounts and under conditions which allow for the reduction and subsequent oxidation of disulfide bonds.

6. The method of claim 5, wherein the denaturation buffer comprises about 1 to about 4 M urea, about 1 mM to about 75 mM sodium borate, about 0.5 M to about 3 M sodium chloride, about 10% to about 30% ethanol and about 0.5- to about 7-fold molar excess of dithiothreitol.

7. The method of claim 6, wherein the denaturation buffer comprises about 1.5 M to about 3 M urea, about 3 to about 50 mM sodium borate, about 1 M to about 1.5 M sodium chloride, about 15% to about 25% ethanol, and about an equimolar to about a 5-fold molar excess of dithiothreitol.

8. The method of claim 1, wherein the hydrophobic interaction chromatography is performed using a polyethyleneamine matrix.

9. The method of claim 1, wherein the hydrophobic interaction chromatography is performed using a butyl- or phenyl-substituted poly(methacrylate) matrix.

10. The method of claim 1, wherein the reverse phase high performance liquid chromatography is performed using a $C_8$ silica-derivatized resin.

11. The method of claim 1, wherein the IGF is IGF-I.

12. The method of claim 1, wherein the IGF is IGF-II.

13. A method for isolating an authentic, properly folded insulin-like growth factor (IGF) polypeptide from a medium into which the IGF polypeptide has been secreted by *Pichia*

*pastoris* cells expressing the IGF polypeptide, wherein the method comprises:

(a) performing a cation exchange chromatography with the medium to obtain a partially purified IGF mixture;

(b) denaturing and renaturing partially purified IGF species;

(c) subjecting renatured IGF species to hydrophobic interaction chromatography; and (d) performing reverse phase high performance liquid chromatography to obtain a further purified IGF mixture, wherein the further purified IGF mixture has a greater amount of authentic, properly folded IGF than the partially purified IGF mixture, and further wherein only one cation exchange step is performed in the method.

14. The method of claim 13, wherein the method further comprises raising the pH of the yeast cell medium which comprises yeast cells to about pH 8 to about pH 12, prior to the first cation exchange chromatography.

15. The method of claim 14, wherein the method comprises raising the pH of the yeast cell medium which comprises yeast cells to about pH 10 to about pH 11, prior to the first cation exchange chromatography.

16. The method of claim 13, wherein the first cation exchange chromatography is performed using a sulfopropylated matrix.

17. The method of claim 13, wherein the denaturing and renaturing steps are performed together using a denaturation buffer comprising urea, dithiothreitol, alcohol and salt, in sufficient amounts and under conditions which allow for the reduction and subsequent oxidation of disulfide bonds.

18. The method of claim 17, wherein the denaturation buffer comprises about 1 to about 4 M urea, about 1 mM to about 75 mM sodium borate, about 0.5 M to about 3 M sodium chloride, about 10% to about 30% ethanol and about 0.5- to about 7-fold molar excess of dithiothreitol.

19. The method of claim 18, wherein the denaturation buffer comprises about 1.5 M to about 3 M urea, about 3 to about 50 mM sodium borate, about 1 M to about 1.5 M sodium chloride, about 15% to about 25% ethanol, and about an equimolar to about a 5-fold molar excess of dithiothreitol.

20. The method of claim 13, wherein the hydrophobic interaction chromatography is performed using a polyethyleneamine matrix.

21. The method of claim 6, wherein the hydrophobic interaction chromatography is performed using a butyl- or phenyl-substituted poly(methacrylate) matrix.

22. The method of claim 13, wherein the reverse phase high performance liquid chromatography is performed using a $C_4$ to $C_{10}$ silica-derivatized resin.

23. The method of claim 13, wherein the IGF is IGF-I or an analog thereof.

24. The method of claim 23, wherein the IGF is IGF-I.

* * * * *